US012299192B2

(12) United States Patent
Asher et al.

(10) Patent No.: US 12,299,192 B2
(45) Date of Patent: May 13, 2025

(54) VISUAL ASSISTANCE

(71) Applicant: UNIVERSITY OF ESSEX ENTERPRISES LIMITED, Essex (GB)

(72) Inventors: Jordi Miriam Asher, Essex (GB); Paul Barry Hibbard, Essex (GB)

(73) Assignee: UNIVERSITY OF ESSEX ENTERPRISES LIMITED, Essex (GB)

(*) Notice: Subject to any disclaimer, the term of this patent is extended or adjusted under 35 U.S.C. 154(b) by 0 days.

(21) Appl. No.: 18/002,936

(22) PCT Filed: Jun. 22, 2021

(86) PCT No.: PCT/GB2021/051584
§ 371 (c)(1),
(2) Date: Dec. 22, 2022

(87) PCT Pub. No.: WO2021/260368
PCT Pub. Date: Dec. 30, 2021

(65) Prior Publication Data
US 2023/0244307 A1 Aug. 3, 2023

(30) Foreign Application Priority Data
Jun. 23, 2020 (GB) .................... 2009562

(51) Int. Cl.
*G06F 3/01* (2006.01)
*G02B 27/01* (2006.01)
(52) U.S. Cl.
CPC ......... *G06F 3/013* (2013.01); *G02B 27/0101* (2013.01); *G02B 27/017* (2013.01);
(Continued)

(58) Field of Classification Search
CPC ... G06F 3/013; G02B 27/0101; G02B 27/017; G02B 27/0179; G02B 2027/0134; G02B 2027/014; G02B 2027/0187
(Continued)

(56) References Cited

U.S. PATENT DOCUMENTS

2012/0249741 A1* 10/2012 Maciocci ............. G06T 19/006
348/51
2015/0002642 A1* 1/2015 Dressler ................ G06T 3/00
348/51
(Continued)

FOREIGN PATENT DOCUMENTS

| CA | 2953335 C | * | 1/2021 | ......... G02B 27/0093 |
| GB | 2548718 | | 9/2017 | |
| WO | WO 2016/182514 | | 11/2016 | |

OTHER PUBLICATIONS

International Search Report and Written Opinion for International (PCT) Patent Application No. PCT/GB2021/051584, dated Sep. 30, 2021, 10 pages.
(Continued)

*Primary Examiner* — Kwin Xie
(74) *Attorney, Agent, or Firm* — Sheridan Ross PC

(57) ABSTRACT

A method, apparatus and computer program are disclosed. A method comprises selecting, from image data associated with an image of a scene, a subset of image data indicative of characteristics of the scene in at least one obscured region in a visual field of a viewer where the visual field is obscured; and displaying at least one viewer support image, generated based on the selected subset of image data, on at least one display screen located in the visual field; whereby the viewer support image is displayed on the display screen such that the viewer support image appears in a predetermined area in the visual field spaced apart from the obscured region in the visual field.

15 Claims, 10 Drawing Sheets

(52) U.S. Cl.
CPC .. *G02B 27/0179* (2013.01); *G02B 2027/0134* (2013.01); *G02B 2027/014* (2013.01); *G02B 2027/0187* (2013.01)

(58) Field of Classification Search
USPC .................................................. 345/156–169
See application file for complete search history.

(56) References Cited

U.S. PATENT DOCUMENTS

| | | |
|---|---|---|
| 2016/0260261 A1* | 9/2016 | Hsu ........................ G02B 27/01 |
| 2018/0125716 A1 | 5/2018 | Cho et al. |
| 2018/0249151 A1 | 8/2018 | Freeman et al. |
| 2019/0114921 A1 | 4/2019 | Cazzoli |
| 2020/0082600 A1 | 3/2020 | Jones et al. |
| 2021/0290053 A1* | 9/2021 | Tran ................... G02B 27/0093 |

OTHER PUBLICATIONS

Search Report for United Kingdom Patent Application No. GB2009562.6, dated Dec. 10, 2020, 2 pages.
International Preliminary Report on Patentability for International (PCT) Patent Application No. PCT/GB2021/051584, dated Dec. 13, 2022, 7 pages.

* cited by examiner

VISUAL ASSISTANCE

CROSS REFERENCE TO RELATED APPLICATIONS

This application is a national stage application under 35 U.S.C. 371 and claims the benefit of PCT Application No. PCT/GB2021/051584 having an international filing date of 22 Jun. 2021, which designated the United States, which PCT application claimed the benefit of Great Britain Patent Application No. 2009562.6 filed 23 Jun. 2020, the disclosures of each of which are incorporated herein by reference in their entireties.

The present invention relates to a method and apparatus that helps provide a viewer of a scene with a visual aid. In particular, but not exclusively, the present invention relates to a method and apparatus to provide a viewer support image on a display screen that can be viewed by a viewer of a scene and that contains characteristics about the scene in an obscured region in a visual field of the viewer.

It is known that from time to time it is helpful for human or animal users to have a clear or meaningful sight of a real scene. Such a view can on occasion be obscured in some way. For example, an object can be placed in a position that covers part of a scene. Alternatively, a health problem may interfere with a proper functioning of an eye.

It is also known that on occasion that a human or animal viewer may wish to view a non-real scene such as a room or space generated via a computer program. Obscured parts of a scene generated in this way can prevent enjoyment or lead to risk.

In terms of possible health problems that might cause a region of a scene to be obscured these can be congenital or can be caused by a life changing event. For example, every year, around 152,000 people in the UK suffer from a stroke (more than one every five minutes) and there are around 17 million first-time cases across the globe. There are around 1.2 million stroke survivors in the UK, and there are around 80 million stroke survivors across the globe. Visual problems are some of the most common and most debilitating consequences of stroke, second only to weakness in the arms or legs. Visual problems include loss of some area of the visual field. Visual field defects are estimated to affect between 20% and 57% of people who have had a stroke. These visual problems are thought to be underreported, such that the prevalence is likely higher than this estimate. The extent of visual field loss varies between individuals. If this affects one half of the visual field, it is referred to as hemianopia. If this is the same side for each eye, it is referred to as homonymous hemianopia.

In contrast to the intensive therapies available for stroke patients with damage to the motor cortex, cortical damage in the visual cortex is considered permanent, and there are only limited treatments that can help restore lost vision. Care for stroke survivors who experience visual problems is thus very limited. The impact of sight loss, whether from stroke or other causes, is extremely disruptive to everyday life, severely impairing reading, mobility and independence, ability to participate in rehabilitation, and creating depression and anxiety. Interventions that do exist can be divided into restitution, compensation and substitution.

Restitution is the attempt to help restore the absent visual field. These interventions include perceptual training—repetitive viewing and responding to simple visual stimuli, with a view to reducing the size of the lost field or increasing contrast sensitivity where it has been reduced. Training is also used in order to improve binocular fusion, which can be impaired as a result of the visual field loss, leading to double-vision and a lack of binocular depth perception. Restitution also includes the repeated stimulation of the impaired visual field, in an attempt to reactivate the corresponding visual areas of the brain. While there have been some promising results from these studies, at present there is insufficient evidence to draw conclusions about their effectiveness. As such, restitutive therapies do not provide a solution for those people currently living with the effects of visual field loss.

Compensation interventions are targeted not at reducing the visual field deficits in any way, but rather at training people to maximise the usefulness of their remaining vision. This includes training on making rapid, saccadic eye movements, visual search strategies, eye-movements for reading and new strategies of making use of cues such as colour in everyday activities. The focus of all of these is to change the strategies developed through a lifetime of unimpaired vision so that they can be optimised for that person's new visual field.

Substitution interventions make use of optical devices or modifications of the environment to improve visual functioning. These include the use of optical prisms within spectacles which act to shift the visual field and typoscopes to provide a guide to eye movements to facilitate reading. However, substitution based on fixed, simple optics such as in the form of Fresnel prisms can cause several problems. For example, the devices can create visual distortions created by prism optics, a disjointed visual field, incorrect mapping between visual field location and visual direction, loss of some visual information through apical scotoma, potential diplopia and visual confusion when prisms are used for visual field expansion. As such there is little evidence that prisms provide an effective substitution. At best, there is evidence that, if anything, prisms do not have an effect on measures of everyday living (including reading), or quality of life, although there is some evidence for an improvement in scanning abilities. Of more concern, there is some evidence for adverse effects, including headaches. In addition, the effect of fixed, simple optics is always present in the visual field and cannot be switched on and off or re-sized.

It is an aim of the present invention to at least partly mitigate at least one of the above-mentioned problems.

It is an aim of certain embodiments of the present invention to help provide a viewer of a scene with a visual aid.

It is an aim of certain embodiments of the present invention to help provide a viewer of a scene with an image that contains information about the scene located in an obscured region of the viewer's visual field.

It is an aim of certain embodiments of the present invention to provide a viewer with a visual aid that helps to provide the viewer with information regarding characteristics of a real-life scene or a computer generated (i.e. virtual) scene that are obscured from view.

It is an aim of certain embodiments of the present invention to help provide a viewer of a scene with an image in a visual field of the viewer whilst helping to limit optical distortion of the viewer's visual field and helping to prevent visual confusion.

It is an aim of certain embodiments of the present invention to help provide a viewer with an image of a scene that is indicative of characteristics of the scene in an obscured region in the viewer's field of view and that may be seen as a distinct object with a clearly specified location in 3D space. This is of benefit when compared with the combination of remapping of the field, and visual confusion, which characterise the effects of prisms.

It is an aim of certain embodiments of the present invention to help provide a viewer of a scene with an image of a scene in their visual field with a contrast, sharpness, luminance, transparency, size and position that can be manipulated in real time. This helps to allow both the display screen and the real world to be seen in the same visual direction (and without spatial confusion since binocular disparity will unambiguously define the location of the screen in 3D space).

According to a first aspect of the present invention there is provided a method for providing a viewer of a scene with a visual aid, comprising the steps of: selecting, from image data associated with an image of a scene, a subset of image data indicative of characteristics of the scene in at least one obscured region in a visual field of a viewer where the visual field is obscured; and displaying at least one viewer support image, generated based on the selected subset of image data, on at least one display screen located in the visual field; whereby the viewer support image is displayed on the display screen such that the viewer support image appears in a predetermined area in the visual field spaced apart from the obscured region in the visual field.

Aptly the at least one display screen is arranged to provide a stereoscopic display screen.

Aptly the obscured region is a blurred region or a blind region in the visual field.

Aptly the method further comprising determining the predetermined area responsive to a preselected input of the viewer.

Aptly the obscured region in the visual field is a visually impaired region present via a sight defect of the viewer.

Aptly for each respective viewer, each obscured region is at a constant location in the visual field.

Aptly the method further comprising selecting the subset of image data by selecting image data indicative of characteristics of the scene in the obscured region and in at least one surrounding region in the visual field that at least partially surrounds the obscured region.

Aptly the method further comprising selecting the subset of image data responsive to accessing at least one memory element which stores one or more records representing a set of co-ordinates for the obscured region in the visual field.

Aptly the viewer support image occupies a visible area in the visual field that is 1 to 50% of a total visual field of the viewer.

Aptly a transparency of the viewer support image is adjustable between a value of 0% and 100%.

Aptly a contrast and/or sharpness of the viewer support image is adjustable.

Aptly a visible area, transparency, contrast and/or sharpness of the viewer support image is adjustable by the viewer.

Aptly the visible area, transparency, contrast and/or sharpness of the viewer support image is adjustable by the viewer in real time.

Aptly the visible area, transparency, contrast and/or sharpness of the viewer support image is adjustable via a mobile application and/or device-specific controls of the viewer and/or via hand gestures and/or voice controls of the viewer.

Aptly the method further comprising providing the display screen in front of a viewer via a heads-up display that supports the display screen; and optionally wherein the heads-up display is an augmented reality headset.

Aptly the method further comprising displaying the viewer support image on a first display screen located in front of a left eye of the viewer and a second display screen located in front of a right eye of the viewer; and displaying the viewer support image in a different area of the first and second display screens such that a perception of depth is provided.

Aptly the method further comprising displaying the image of the scene on the display screen such that the image occupies substantially all of the visual field; and overlaying the viewer support image on the displayed image of the scene.

Aptly the method further comprising displaying the viewer support image on at least one partially transparent display screen such that a remaining visual field outside of an area associated with the viewer support image in the visual field is provided via a direct line-of-sight between an eye of the viewer and the scene.

Aptly the scene is a real scene or a virtual scene.

Aptly the method further comprising capturing at least one image of a scene via at least one image capture device; and selecting the subset of image data from image data associated with the captured image.

Aptly the at least one captured image is a video feed comprising a plurality of captured images and the viewer support image displayed on the display screen is updated frame-by-frame for each captured image.

Aptly the image capture device is a video camera, a digital camera or the like.

Aptly the method further comprising providing the image capture device via a headset that supports the image capture device and that is secured to a head of the viewer.

According to a second aspect of the present invention there is provided apparatus for providing a viewer of a scene with a visual aid, comprising: at least one processor configured to select, from image data associated with an image of a scene, a subset of image data indicative of characteristics of the scene in at least one obscured region in a visual field of a viewer where the visual field is obscured; and at least one display screen locatable in the visual field that displays at least one viewer support image, generated based on the selected subset of image data; whereby the viewer support image is displayed on the display screen such that the viewer support image appears in a predetermined area in the visual field spaced apart from the obscured region in the visual field.

Aptly the at least one display screen is arranged to provide a stereoscopic display screen.

Aptly the obscured region is a blurred region or a blind region in the visual field.

Aptly the processor is configured to determine the predetermined area responsive to a preselected input of the viewer.

Aptly the obscured region in the visual field is a visually impaired region present via a sight defect of the viewer.

Aptly for each respective viewer, each obscured region is at a constant location in the visual field.

Aptly the processor is configured to select a subset of image data indicative of characteristics of the scene in the obscured region and in at least one surrounding region in the visual field that at least partially surrounds the obscured region.

Aptly the apparatus further comprising at least one memory element which stores one or more records representing a set of co-ordinates for the obscured region in the visual field; and wherein the processor is configured to select the subset of image data responsive to accessing the memory element.

Aptly the viewer support image occupies a visible area in the visual field that is 1 to 50% of a total visual field of the viewer.

Aptly a transparency of the viewer support image is adjustable between a value of 0% and 100%.

Aptly a contrast and/or sharpness of the viewer support image is adjustable.

Aptly a visible area, transparency, contrast and/or sharpness of the viewer support image is adjustable by the viewer.

Aptly the visible area, transparency, contrast and/or sharpness of the viewer support image is adjustable by the viewer in real time.

Aptly the visible area, transparency, contrast and/or sharpness of the viewer support image is adjustable via a mobile application and/or device-specific controls of the viewer and/or via hand gestures and/or voice controls of the viewer.

Aptly the display screen is provided in front of a viewer via a heads-up display that supports the display screen; and optionally wherein the heads-up display is an augmented reality headset.

Aptly the viewer support image is displayed on a first display screen located in front of a left eye of the viewer and a second display screen located in front of a right eye of the viewer; and wherein the viewer support image is in a different area of the first and second display screens such that a perception of depth is provided.

Aptly the display screen is at least partially transparent.

Aptly the display screen displays the image of the scene such that the image occupies substantially all of the visual field; and wherein the viewer support image is overlaid on the displayed image of the scene.

Aptly the display screen is at least partially transparent and displays the viewer support image such that a remaining visual field outside of an area associated with the viewer support image in the visual field is provided via a direct line-of-sight between an eye of the viewer and the scene.

Aptly the scene is a real scene or a virtual scene.

Aptly the apparatus further comprising at least one image capture device configured to capture at least one image of a scene; wherein the processor is configured to select the subset of image data from image data associated with the captured image.

Aptly the at least one captured image is a video feed comprising a plurality of captured images and wherein optionally the viewer support image displayed on the display screen is updated frame-by-frame for each captured image.

Aptly the image capture device is a video camera, a digital camera or the like.

Aptly the image capture device is provided via a headset that supports the image capture device and that is secured to a head of the viewer.

According to a third aspect of the present invention there is provided a computer program comprising instructions which, when the program is executed by a computer, cause the computer to carry out the method according to the first aspect of the present invention.

Certain embodiments of the present invention help provide a viewer of a scene with a visual aid.

Certain embodiments of the present invention help provide a viewer of a scene with an image that contains information about the scene that appears in an obscured region of the viewer's visual field.

Certain embodiments of the present invention help provide a viewer of a scene with an image in a visual field of the viewer that helps to limit optical distortion of the viewer's visual field and thus helps to prevent visual confusion.

Certain embodiments of the present invention help provide a viewer with an image of a scene that is indicative of characteristics of the scene in an obscured region in the viewer's field of view and that may be seen as a distinct object with a clearly specified location in 3D space.

This is of benefit when compared with the combination of remapping of the field, and visual confusion, which characterise the effects of prisms.

Certain embodiments of the present invention help provide a viewer of a scene with an image of a scene in their visual field with a contrast, sharpness, luminance, transparency, size and position that can be manipulated in real time. This helps to allow both the display screen and the real world to be seen in the same visual direction (and without spatial confusion since binocular disparity will unambiguously define the location of the screen in 3D space).

Certain embodiments of the present invention provide a viewer with a visual aid that helps to provide the viewer with information regarding characteristics of a real-life scene or a computer generated (i.e. virtual) scene that are obscured from view.

Certain embodiments of the present invention will now be described hereinafter, by way of example only, with reference to the accompanying drawings in which.

In the drawings like reference numerals refer to like parts.

Figure 1:
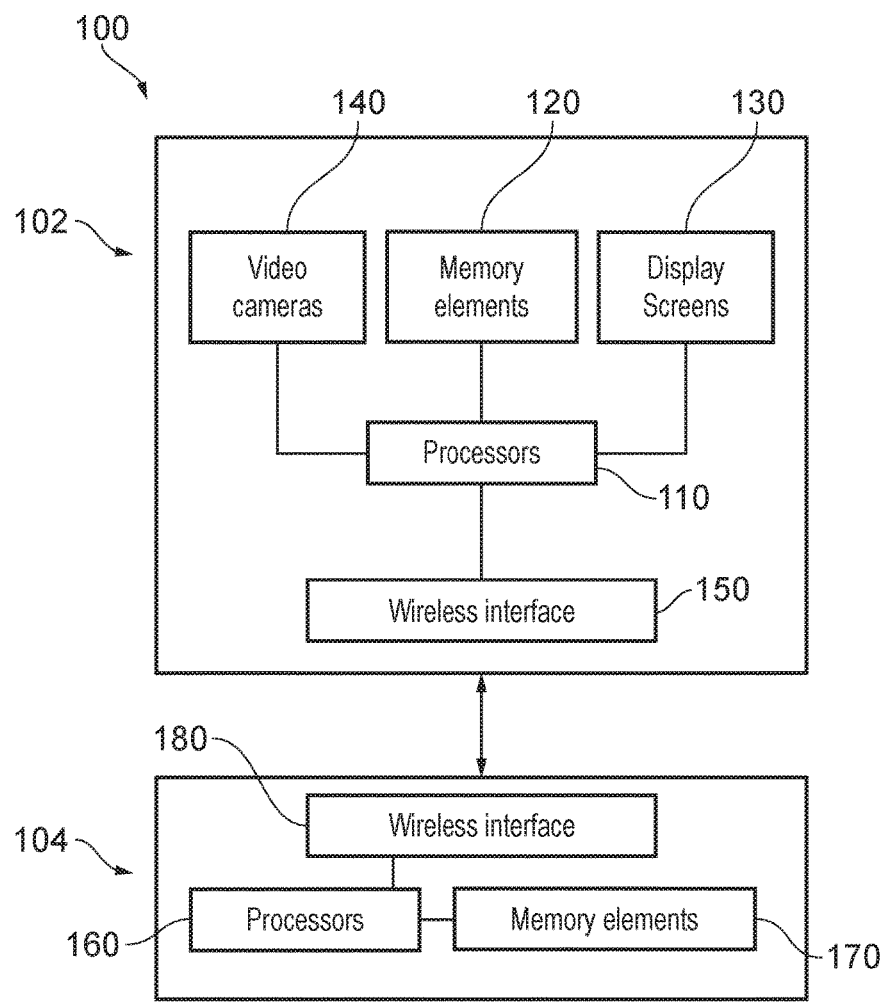
FIG. 1 illustrates a system for providing a visual aid.

FIG. 1 illustrates certain elements of a system 100 that can provide a visual aid. The system 100 includes an augmented reality headset 102 and a mobile device 104. The augmented reality headset 102 includes multiple processors 110, multiple memory elements 120, two display screens 130, three video cameras 140 and a wireless interface 150. The headset 102 may comprise additional features such as a head support, lenses, a power supply and the like as will be apparent to a person skilled in the art although these have not been illustrated for the purposes of understanding the invention. As an example, the headset 102 may be a Microsoft HoloLens 2 or a similar augmented reality headset as will be appreciated by a person of skill in the art.

The headset 102 illustrated in FIG. 1 can be secured to a head of a viewer such that a first display screen 130 is located in front of a left eye of a viewer and a second display screen 130 is located in front of a right eye of a viewer. However, according to certain other embodiments of the present invention only one display screen may be used which may for example be a unitary display screen that extends in front of only one eye or extends in front of both the left and right eyes of the viewer. The display screens 130 can display images to the viewer such that the images appear in a visual field of the viewer and the viewer is therefore able to observe the displayed images. In the system illustrated in and disclosed with respect to FIG. 1 the display screens are arranged to display different images to the viewer's left and right eye such that they together they form a stereoscopic display screen. This helps allow the two display screens to convey depth perception to the viewer by means of stereopsis for binocular vision. However, it will be appreciated that other types of display screens may be used in accordance with certain other embodiments of the present invention. For example, in certain embodiments only one display screen may be provided for monocular vision. This may be necessary such as when the viewer only has vision via one eye. The display screens may be LED display screens, LCD display screens, QLED display screens, OLED display screens or the like. The display screens illustrated in FIG. 1 are partially transparent such that the viewer is able to view a scene on a distal side of the display screens directly. In other words, light from the real-life scene may pass through the display screens and into the viewer's eyes. Alternatively, according to certain other embodiments of the present invention, the display screens may not be transparent but may be translucent or opaque such that substantially no light is allowed to pass through the display screens. In these alternative embodiments, an image of the real-life scene would instead be displayed to the viewer on the display screens such that the viewer's visual field is predominantly occupied by the image of the scene on the display screens. The viewer then views the scene by looking at the display screens. As a still further alternative, an image of a computer-generated or virtual scene may be displayed on the display screens instead of an image of a real-life scene. Such computer-generated scenes may be used for example when training a viewer on how to use an augmented reality headset or display screen that is configured to display a viewer support image.

In the system shown in FIG. 1, the video cameras 140 are secured to the headset 102 such that an image of a scene being viewed by a viewer can be captured. The video cameras are an example of an image capture device. Alternatively, the image capture devices 140 may be any other type of camera that can capture images of a scene as will be appreciated by a person of skill in the art. Furthermore, it will be appreciated that the separate image capture devices on the headset do not necessarily need to be the same type of image capture device. The video cameras 140 are positioned on the headset such that a field of view captured by the video cameras substantially corresponds to a visual field of the viewer. The video cameras 140 are able to capture images of a scene present in the field of view of the video cameras.

The video cameras 140 may then transmit the image data associated with a captured image to the processors 110 in order for the processors to manipulate the image data and/or transmit the image data to the display screen so that all or part of the captured image may be displayed on one display screen or both display screens 130. It will be appreciated by a person skilled in the art that the processors that perform the image data manipulation and/or transmit the image data may not necessarily be processors that are separate from the video cameras 140 as illustrated in FIG. 1 but may be processors that are integral with any of the video cameras 140 or that are processors which are part of the mobile device 104 as will be discussed in more detail below. It will also be appreciated that any number of video cameras may be used, including only one video camera, in certain other embodiments of the present invention. For example, a single video camera located approximately midway between the left and right eye of the viewer may be utilised or a video camera associated with each eye of a viewer wearing a headset may be utilised. In the system illustrated in FIG. 1 one video camera is located proximate to a left eye, one video camera is located proximate to a right eye and one video camera is located approximately midway between the left and right eyes. Furthermore, whilst the system illustrated in FIG. 1 has been described with respect to captured images of a real scene being provided by video cameras, it will be appreciated that certain other embodiments of the present invention may not require a video camera or any other image capture device. For example, in certain other embodiments of the present invention the viewer may be viewing a virtual scene (for example through a VR headset) and an image associated with the virtual scene may not necessarily need to be captured by any image capture device but may be directly rendered on the display via a computer program that can be executed on a computer. In other words, the viewer would view a computer generated image of a scene.

As described above, the headset 102 illustrated in FIG. 1 has multiple processors 110 and includes a CPU and a GPU. According to certain other embodiments of the present invention, however the headset may only comprise a single processor such as a CPU or a GPU. It will nevertheless be appreciated that any number of processors may be utilised, including only one processor, as will be understood by a person skilled in the art. The processors 110 may receive image data associated with an image captured via by one (or more) of the video cameras 140 and manipulate the image data to create a viewer support image. For example, the processor 110 may communicate with a memory element 120 in order to access one or more records that indicates a set of co-ordinates associated with an obscured region present in a visual field of the viewer. For example, the obscured region may be a region where the visual field of the viewer is visually impaired. These co-ordinates may be determined via a standard optometric test such as a perimetry assessment that determines the locations in a viewer's visual field that are impaired for that particular viewer. These determined co-ordinates are then stored in the memory element. Alternatively, the assessment of the viewer's impaired region in their visual field may be determined by using the augmented reality headset and carrying out an optometric test using the headset. In certain other embodiments of the present invention the viewer may instead specifically select an area of their visual field that is obscured and set this region as the obscured region. This obscured region may be set and re-set according to the needs of that particular viewer. For example, a viewer may specify a region of the scene that is out of view or non-visible and set that region as the obscured region.

The processors 110 select a subset of image data associated with the captured image that is indicative of the characteristics of the scene in the obscured region. The subset of image data is then used to generate a viewer support image. It will thus be appreciated that the viewer support image contains visual information about the scene in an area of the visual field of the viewer which is not visible to the viewer or that the viewer cannot clearly see due to their visual impairment. The viewer support image can therefore act as a visual aid. It will also be appreciated by a person skilled in the art that the video cameras 140 and/or the processors 110 and/or the display screens 130 may assist in generation of the viewer support image. The generated viewer support image may be displayed on each of the display screens 130 so that it is viewable by the viewer in their visual field. For example, the viewer support image is displayed in an area of the visual field that is spaced apart from the area associated with the obscured region of the visual field. The remainder of the visual field outside of the area associated with the viewer support image may be provided via a direct line-of-sight between the viewer's eye and the scene in which case the display screens will be at least partially transparent to allow light from the scene to pass through the display screens and enter the viewer's eyes to thereby impinge on the viewer's retinas. This configuration may be referred to as optical see through and/or a mixed reality view. Alternatively, the original image of the scene (or a marginally re-sized version thereof) may be displayed on substantially the full extent of the display screens located in front of the viewer's eyes such that the viewer observes an image of the scene on the display screens instead of directly viewing the scene itself. In this scenario, the viewer support image may be overlaid on the original image such that the remainder of the visual field outside of the area associated with the viewer support image is provided by the original captured image displayed on the display screens. This configuration may be referred to as video see through and/or a virtual reality view.

A computer program comprising instructions may be executed by a computer (for example the headset 102) to carry out a method involving the steps of selecting, from an image of the scene, the subset of image data indicative of characteristics of the scene in the obscured region in the visual field of a viewer. The method may also involve displaying a viewer support image on the display screens located in the visual field of the viewer in a predetermined area spaced apart from the obscured region.

Turning to the mobile device 104 illustrated in FIG. 1 it will be seen that the mobile device also comprises multiple processors 160, multiple memory elements 170 and a wireless interface 180. It will be understood that the mobile device may also include one or more display screens (not shown). Additionally, the mobile device 104 may include additional features such as a power supply, a keypad, a touch screen and the like as will be apparent to a person skilled in the art although these have not been illustrated for the purposes of understanding the invention. In the system illustrated in FIG. 1, the mobile device 104 is a mobile phone. However, according to certain other embodiments of the present invention the mobile device may instead be a tablet computer, a laptop, a PC or the like. The mobile device 104 can be used by a viewer wearing the headset 102 to control certain aspects of the viewer support image displayed on the display screens 130. For example, a memory element 170 of the mobile device may store a mobile application (not shown) that when run on a processor 160 enable the viewer to interact with the mobile application in order to control the viewer support image. For example, in the system illustrated in FIG. 1, the viewer may provide a user input via a touch screen (not shown) of the mobile device or via a keypad (not shown) in order to interact with the mobile application. Other user inputs will also be appreciated by a person skilled in the art such as voice controls and/or hand gestures which may be detected by the video cameras 140 associated with the headset 102 and/or an imaging device (not shown) associated with the mobile device 104. Upon entering a user input, the processor 160 causes the mobile device to transmit a command to the headset via wireless interface 180. The command is received by corresponding wireless interface 150 of the headset 102 before being passed to processors 110 that implement the command. Furthermore, it will be appreciated by a person skilled in the art that any communication methodology may be used between the headset and the mobile device. For example, the headset 102 and the mobile device 104 may be connected via a wired interface.

The user input provided by the viewer may cause various adjustments to the viewer support image. For example, the viewer may adjust a position of the viewer support image in the visual field of the viewer which will consequently cause the position on which the image is displayed on the display screens 130 to be adjusted.

The viewer may also adjust the size of the viewer support image. In other words, the viewer may adjust a visible area of the viewer support image in the visual field of the viewer. For example, the viewer may adjust the area occupied by the support image between a value of 1% to 50% of a total visual field of the viewer. For example, where the original width and height of the viewer support image (as captured on a camera's imaging sensor) is $W_0$ and $H_0$ pixels, respectively, and the desired width and height (of the viewer support image) is $W_1$ and $H_1$, respectively, bilinear interpolation can be used whereby each pixel position $(x_i, y_i)$ in the re-sized image is used to calculate the pixel positions in the original image $(x_j, y_j)$ via the following equations:

$$x_j = \frac{W_0 x_i}{W_1} \quad y_j = \frac{H_0 y_i}{H_1}$$

Then Using the Following Equations:

$$x_0 = \lfloor x_j \rfloor \; x_1 = x_0 + 1 \; y_0 = \lfloor y_j \rfloor \; y_1 = y_0 + 1$$

and the distances $p = y_j - y_0$ and $q = x_j - x_0$, the pixel intensity value in the resized image, $I_1(x_i, y_i)$ is determined from the original image intensity $I_0$ as follows:

$$I_1(x_i, y_i) = (1-p)(1-q)I_0(x_0, y_0) + (1-p)qI_0(x_1, y_0) + (1-q)pI_0(x_0, y_1) + pqI_0(x_1, y_1)$$

It will be appreciated that other algorithms for resizing an image may be used.

The viewer may also enhance the edges of the viewer support image. For example, the edges may be enhanced using a sharpening algorithm such as unsharp masking. For example, the original viewer support image, O, may be modified to create a blurred version of the support image, B, by convolving it with a Gaussian filter with a standard deviation, s. Thereby, an initial sharpened image, $S_0$ can be obtained via $S_0 = O + A(O - B)$, where A is the amount of enhancement. A final sharpened image, S, is then obtained by applying a threshold, T. For example, for each pixel in the image the difference between the value of the pixel in the original image and the initial sharpened image is calculated and if the size of the difference is greater than the threshold value, T, then the value of that pixel in the final sharpened image, S, is the value present in $S_0$. Otherwise, the value of that pixel present in the original image, O, is used in the sharpened image, S.

The contrast of the viewer support image may also be adjusted. One example measure of contrast is Michelson contrast which is the difference in luminance between the brightest and darkest pixel in the image. However, it will be appreciated that other contrast metrics are available. The lowest and highest intensity values are designated as $L_{MIN}$ and $L_{MAX}$, respectively. In order to help maximise the contrast of the support image the luminance intensity values are scaled such that the darkest possible pixel intensity has a value of 0 and the highest possible pixel intensity has a value of 1. Then, for each pixel, its original luminance intensity $L_0$ is rescaled to a new value $L_1$ following the equation:

$$L_1 = \frac{L_0 - L_{MIN}}{L_{MAX} - L_{MIN}}$$

The overall contrast and luminance in the viewer support image may then be modulated as follows. If the original viewer support image is designated as $P_0$ and the mean value of all the pixels in $P_0$ is $P_{mean}$, then the luminance and contrast may be varied to produce a modulated viewer support image, $P_1$, according to the following equation:

$$P_1 = M + C(P_0 - P_{mean})$$

where M is the mean luminance of the resulting image and C is the contrast gain.

The viewer may also adjust a transparency of the support image between a value of 0% and 100%. This may be desirable as the viewer will then be able to decide when they wish to view either a region of the scene corresponding to the area of their visual field occupied by the viewer support image or the viewer support image or both.

The viewer may also choose to remove the viewer support image from their visual field such that the viewer support image is no longer displayed on the display. This may be desirable for example when the viewer wants to inspect the region of the scene located in the viewer's visual field where the support image is being displayed and that is otherwise obscured by the viewer support image.

Figure 2:
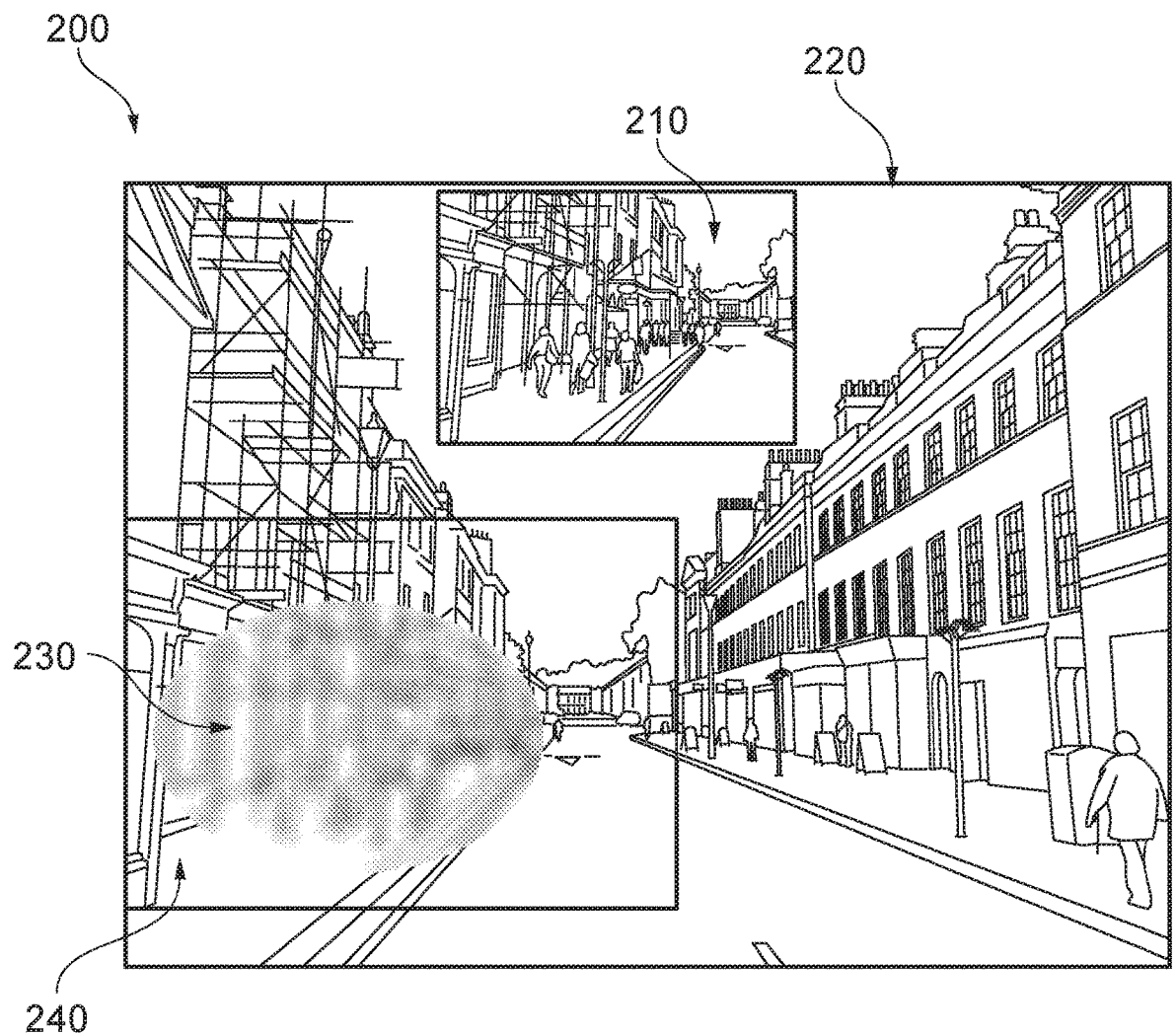
FIG. 2 illustrates a viewer support image displayed in a visual field of a viewer with a sight defect.

FIG. 2 illustrates an exemplary scene 200 that is being viewed by a viewer through a partially transparent display screen and also illustrates how a viewer support image 210 is presented in the visual field 220 of a viewer. For example, in FIG. 2 the viewer support image 210 is being displayed on a single display screen located in front of the viewer's eyes such that the image 210 appears in their visual field. As will be seen from FIG. 2, the viewer support image is displayed such that it appears in an area of the visual field where there are no or only few features of interest. This will often be in the upper half of the visual field however the viewer support image may be displayed at any location according to the needs of a viewer and the position of the support image may be adjusted by the viewer in real-time. The viewer support image 210 appears in a predetermined area in the visual field on the basis that the position of the support image 210 can be determined before it is displayed. For example, the position of the image may be determined by the manufacturer of the headset that includes the displays screen or by the distributor of the software responsible for generating the viewer support image. The position may also be determined by a viewer before the headset is powered on. Nevertheless, it will be understood that the position of the support image is not fixed and the viewer may adjust the position of the support image in real-time. It will also be appreciated that the position may be determined automatically by the software according to the specific characteristics of the scene that the viewer is viewing. This may be referred to as intelligent re-positioning of the viewer support image. For example, the original image of the scene may be analysed via an image analysis algorithm to determine a region or regions of the original image (corresponding substantially to the visual field of the viewer) where there are no or only few features of interest and/or where the viewer's visual field is not obscured. Such image analysis algorithms will be appreciated by a person skilled in the art. The viewer support image can then be displayed in this determined region. Furthermore, using such an image analysis algorithm may result in the viewer support image changing position automatically in real-time as the viewer changes their visual field (for example by rotating their head).

Aptly, the intelligent re-positioning of the viewer support image may be based on the optimal position for the visual field of the user and/or the saliency of the scene.

Figure 10:
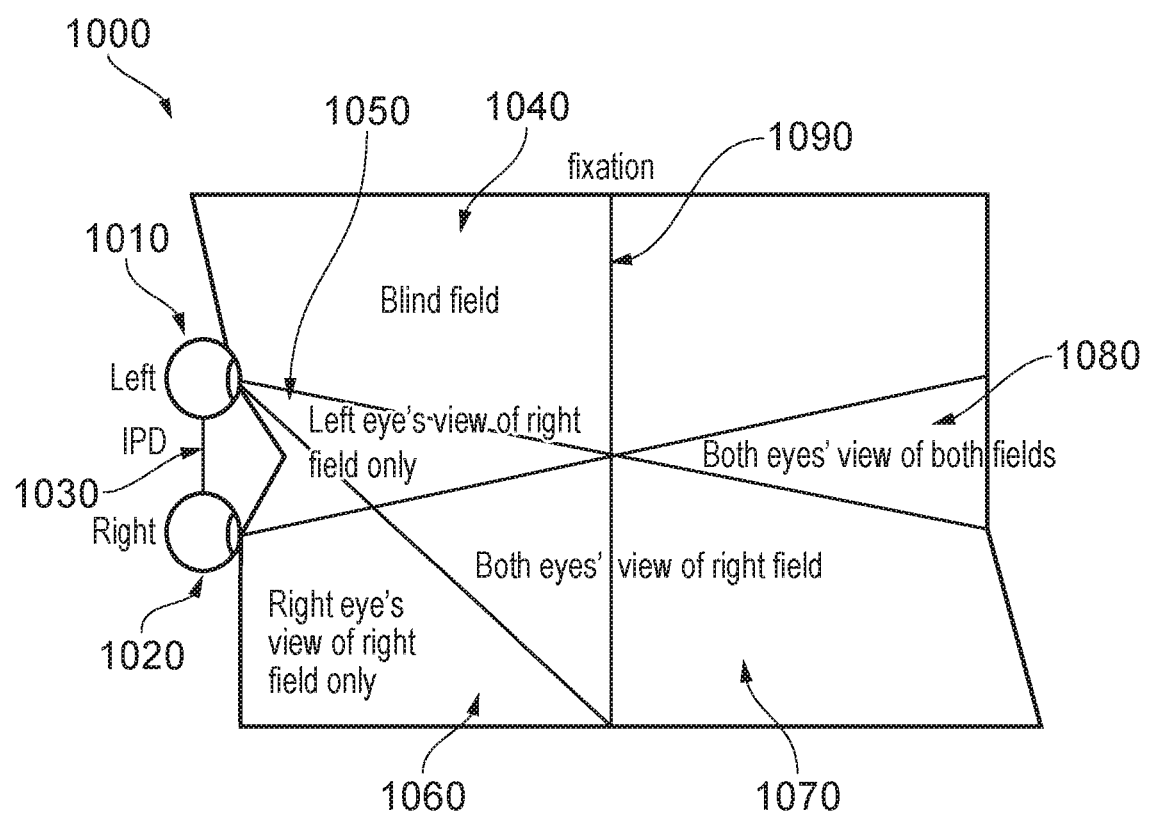
FIG. 10 illustrates an example of a visual field of a viewer with a blind field region.

When intelligently re-positioning the viewer support image based on the remaining field of view of the user, an image analysis algorithm may use parameters such as interpupillary distance (IPD), clinical perimetry and/or volumetric perimetry to establish optimal position(s) in 3D space, based on the users' remaining visual field (that is not obscured by a blind field) as will be appreciated by a person of skill in the art. It will be appreciated that this optimal positioning will be unique for each individual depending on the extent of their field loss both in visual angle and 3D volume. The positioning of the support image will identify areas within 3D perimetry with functional binocular vision, and select appropriate depth of positioning using the IPD as a guide. FIG. 10 illustrates an example visual field 1000 for a viewer having a left eye 1010, a right eye 1020 and an interpupillary distance (IPD) 1030. The viewer has a blind field 1040 (i.e. an obscured region) in their visual field. This is predominantly in the left field of the viewer. The visual field also includes a first region 1050 where the left eye 1010 can see the right field only, a second region 1060 where the right eye 1020 can see the right field only, a third region 1070 where both the left eye 1010 and the right eye 1020 can see the right field and a fourth region 1080 where both the left eye 1010 and the right eye 1020 can see the left field and the right field. Also shown in FIG. 10 is the fixation plane 1090 of the viewer.

When intelligently re-positioning the viewer support image based on the saliency of the scene, the repositioning may use image analysis algorithms to facilitate re-positioning the viewer support image in an optimal location, to avoid obscuring salient targets in the field of view. That is, an image analysis algorithm may be configured to re-position the viewer support image based on characteristics of the scene. For example, this may involve dynamically re-positioning the viewer support image. This dynamic re-positioning may be automatic and occur in real-time. The image analysis algorithms may also be configured to increase the transparency of the viewer support image and/or to temporarily remove the viewer support image according to the characteristics of the scene. It will be appreciated that this approach may prevent the viewer support image obscuring salient objects and features, especially in near space. In more detail, image analysis algorithms may be used to identify when the viewer support image is no longer necessary, can be moved, or can be made more transparent. This may occur, for example, when having a close-range face to face discussion, or when in a cluttered or busy environment. The image analysis algorithms may aptly be configured to determine saliency maps, 3D scene reconstruction, image segmentation, and object, face and scene recognition in order to make a determination of the optimal position of the viewer support image as will be appreciated by a person of skill in the art.

Image saliency algorithms determine regions of the image in which potentially important image features are located. Saliency can be calculated automatically in real time using cascades of linear filtering in a convolutional artificial neural network. This network convolves the video input with linear filters tuned to multiple scales, and to predetermined features (e.g. orientation, colour and brightness). The outputs of these convolutions are then normalised and fed to a second, iterative convolution stag, with inhibitory connections between different image locations, and half-wave rectification of the output of each cycle of convolution. The final saliency map is created by summing the results across scale, performing an additional iterative stage of convolution, and summing the results across multiple features.

3D scene reconstruction, image segmentation and object, scene and face recognition can be performed in real time using suitably trained deep convolutional neural networks. As an example implementation, 3D scene reconstruction, image segmentation and object recognition can be performed using a deep neural network architecture comprising five types of layers: convolutional, batch normalisation, maximum pooling, up-sampling, softmax and skip connections/residual units. A network created from a suitable arrangement of these layers can be trained to estimate the 3D layout of the scene, segment the scene into separate objects, and identify each of the objects, through training on labelled ground-truth data sets. Face and object detection algorithms can also be created by using deep recurrent convolutional neural network architectures, pre-trained using labelled ground-truth data sets.

The viewer support image 210 is displayed such that it appears in an area of the viewer's visual field that is spaced apart from an obscured region 230. The obscured region 230 as illustrated in FIG. 2 corresponds to an area of the viewer's visual field where the viewer's view is impaired. By displaying the support image 210 such that it appears in the visual field in the area shown in FIG. 2, it can therefore be viewed by the viewer and is not itself concealed from view via the obscured region 230. As will be appreciated by a person of skill in the art, the visual field 220 of the viewer is the area that may be viewed by a viewer when the eye is directed forward, including that which is seen with peripheral vision. The visual field may change from viewer to viewer. In the visual field illustrated in FIG. 2, the obscured region 230 appears in the left-hand side of the visual field of the viewer. This is the region in which characteristics of the scene are masked from view of the viewer. It will be appreciated by a person skilled in the art that the sight defect of the viewer may be hemianopia and as such the obscured region 230 may be located at a constant location in the visual field of a viewer. It will also be appreciated that the obscured region 230 illustrated in FIG. 2 is a blurred region and the viewer's eyes may collect light from this region although their sight defect causes the region to be blurred (due to the visual impairment being manifested via a brain injury and not an eye injury). However, according to other sight defects the obscured region may not be blurred but may be a blind region where although the viewer's eyes may be able to collect light from this region, as a result of a brain injury their sight defect causes this region to appear completely concealed in their visual field (i.e. the obscured region may be a blackened or darkened region). It will also be appreciated that other sight defects may arise due to direct injuries to the eyes.

Also illustrated in FIG. 2 is a surrounding region 240 which at least partially surrounds the obscured region in the visual field 220 of the viewer. When a subset of image data is selected from an image of the scene to help generate the viewer support image 210, it can be desirable to select the subset such that characteristics of the scene in both the obscured region 230 and a surrounding region 240 are included. This helps provide the viewer of the scene in FIG. 2 with some context of objects in the scene that are outside the viewer's impaired region and thus helps provide the viewer with a relationship between the objects that the viewer can see in their visual field and those objects in their visual field which they cannot see. As will be understood from FIG. 2, the viewer support image 210 is representative of the region associated with the illustrated boxed area in the lower left-side of the visual field 220 which contains the obscured region 230 and the surrounding region 240 in the viewer's visual field 220. However, it will be appreciated by a person skilled in the art that the surrounding region may not be displayed on a display screen in the viewer's visual field and only an image of the obscured region 230 may be displayed. Furthermore, whilst only one obscured region 230 is illustrated in FIG. 2, it will be appreciated that other viewers may have more than one obscured region in their visual field.

Furthermore, it will be appreciated that whilst a real-life scene is illustrated in FIG. 2, according to certain other embodiments of the present invention the scene may be a computer-generated (i.e. virtual) scene and the viewer may view a computer generated image of the scene. In this case, the viewer may still have an obscured region in their visual field as a result of a sight defect or there may still be regions of the scene that are out of view or non-visible to the viewer. As such, a viewer support image may still be generated based on an image associated with the computer-generated scene in the region that is obscured. This image may then be displayed on a display screen (which may also be displaying the virtual scene) in the viewer's visual field to provide the viewer with a visual aid.

Figure 3:
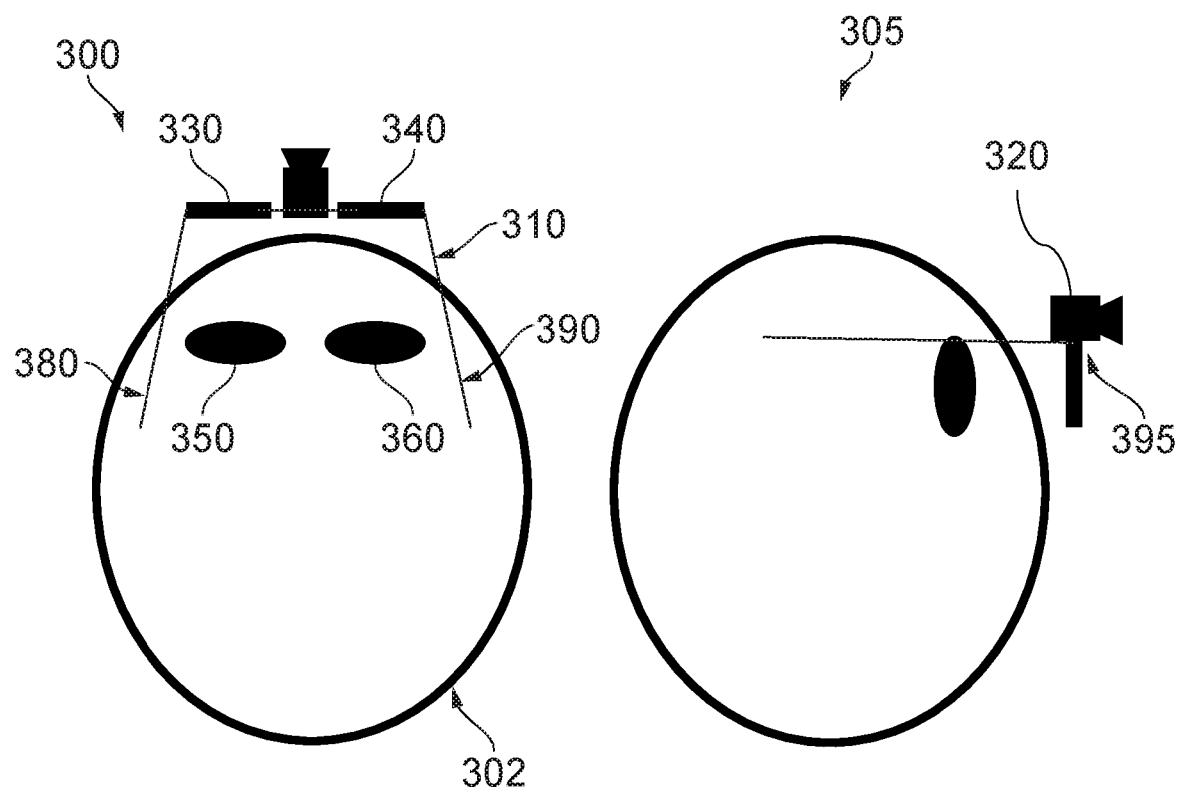
FIG. 3 illustrates a viewer wearing head mounted equipment that can provide a visual aid in real time.

FIG. 3 illustrates a top-view 300 and side-view 305 of a viewer 302 wearing a headset 310 that can provide the viewer with a visual aid in real-time. As illustrated in FIG. 3, the headset 310 includes a single video camera 320 that captures images of a scene, frame by frame, from the view of the viewer 300. The viewer may be a human or animal viewer. The headset 310 also includes a first display screen 330 in front of a left eye 350 of the viewer and a second display screen 340 in front of a right eye 360 of the viewer in the form of a heads up display. The video camera 320 may capture images of the scene and then transmit the image data to a processor (not shown) within the headset 310 for manipulation of the image data. In particular, the processor selects a subset of image data from image data associated with the captured image and that selected subset of image data may then be used to generate a viewer support image. Alternatively, the image data may be transmitted to a mobile device (not shown) and the image data may be manipulated by the mobile device before being sent back to the headset 310 so that a viewer support image can be presented on the display screens 330, 340 based on the subset of image data determined by the mobile device. The process of selecting a subset of image data may be performed for each image such that the viewer support image displayed on the display screens 330, 340 is updated in real-time. The viewer support image may be displayed on either the first display screen 330, the second display screen 340 or both of the first and second displays screens concurrently. As such, the viewer will be able to see the viewer support image in their visual field.

The headset 310 also includes a first supporting arm 380 and a second supporting arm 390 that provides means for securing the headset 310 to the viewer's head. The supporting arms 380, 390 extend from fixing points 395 located proximate a respective display screen 330, 340 and extend along the side of a viewer's head to hook behind a respective ear of the viewer. Alternatively, according to certain other embodiments of the present invention, instead of providing supporting arms a strap may extend from each of the fixing points and extend around a full circumference of the viewer's head to provide a single adjustable supporting strap. It will also be appreciated that any appropriate headset or other device may be used according to certain other embodiments of the present invention.

Figure 4A:
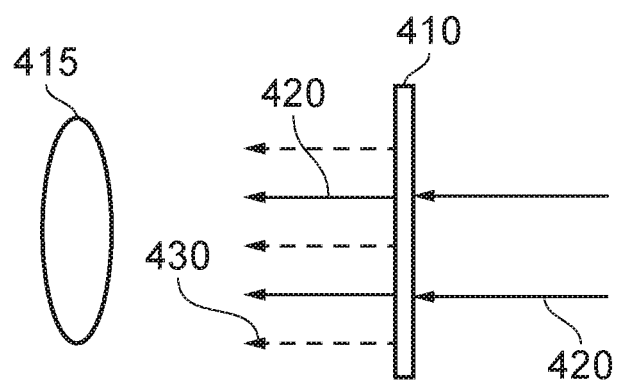
FIG. 4A illustrates an eye of a viewer viewing a real-life scene directly and viewing a visual aid via a display screen.

FIG. 4A illustrates an eye of a viewer viewing a real-life scene directly and viewing a visual aid via a display screen. For example, in FIG. 4A the display screen 410 is partially transparent and allows light to be transmitted through the display screen 410 and thereafter into an eye of a human being 415. A human being is an example of a viewer of a scene. As such, light originating from and/or reflecting from objects contained in the scene being viewed by the viewer may pass through the display screen such that the viewer can view these objects directly. In other words, the viewer has a direct line-of-sight to these objects. The rays of light originating from a part of the scene that the viewer is viewing directly are illustrated in FIG. 4A as solid arrows 420. Additionally, a viewer support image may be displayed on the display screen 410 such that light is also transmitted from the display screen 410 into the eye 415 of the viewer. As such, in addition to viewing objects in the scene directly, the viewer also sees a viewer support image provided by the display screen. The rays of light originating from the display screen 410 are illustrated as dashed lines 430. It will thus be appreciated that the type of display screen illustrated in FIG. 4A helps to provide a mixed reality approach and the viewer is shown only a viewer support image on the display screen whereas the remainder of their visual field is provided via the viewer's direct, unassisted view of the scene.

Figure 4B:
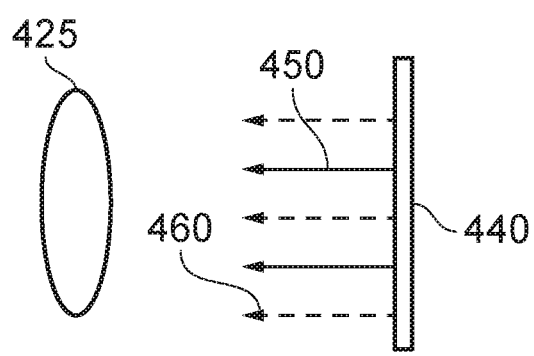
FIG. 4B illustrates an eye of a viewer viewing both a real-life scene and a visual aid via a display screen.

FIG. 4B illustrates an eye 425 of a viewer viewing both a real-life scene and a visual aid via a display screen. For example, in FIG. 4B a display screen 440 is opaque and does not allow light to be transmitted through the display screen 440 and into the viewer's eye 425. Instead, an image of a scene is provided on substantially the full extent of the display screen 440 such that the viewer's visual field is predominantly occupied by the image of the scene displayed on the display. It will thus be appreciated that the viewer views a virtual manifestation of the scene instead of the scene itself. The rays of light originating from the image of the scene presented on the display screen 440 are illustrated as solid lines 450. Additionally, a viewer support image may also be displayed on the display screen 440 such that the viewer support image is overlaid on the original image of the scene. As such, in addition to viewing the image of the full scene, the viewer also sees a viewer support image provided by the display screen 440. The rays of light originating from the display screen 440 in the region associated with the viewer support image are illustrated as dashed lines 460. It will thus be appreciated that the type of display screen illustrated in FIG. 4B helps to provide a virtual reality approach and the viewer is shown both an image of the full scene and an overlaid viewer support image on the display screen simultaneously.

Figure 5:
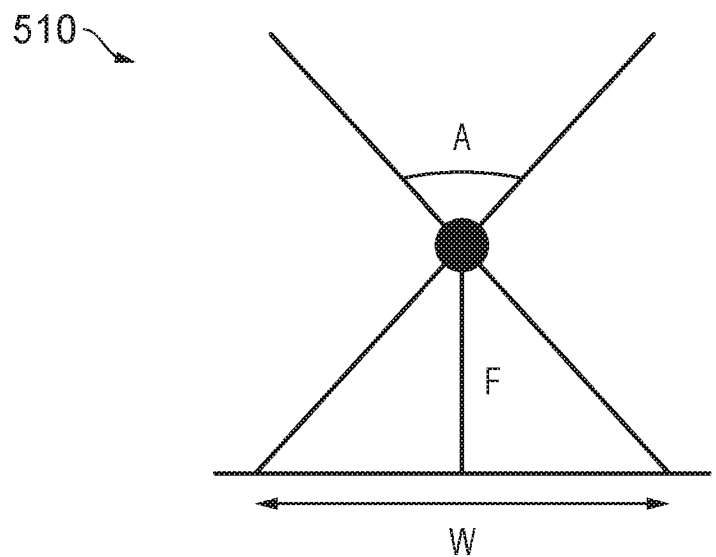
FIG. 5 illustrates a relationship between an angular position of a visual feature in a scene and the position of the visual feature on a sensor of a video camera.
Figure 5:
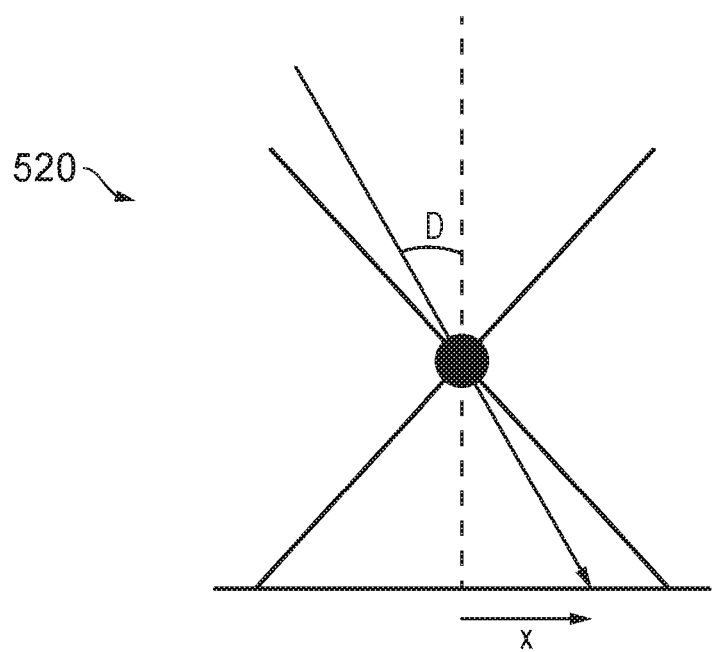

FIG. 5 helps to illustrate a relationship between an angular position of a visual feature in a scene and the position of the visual feature on a sensor of an image capture device. For example, an image capture device may have a focal length F and have a field of view with a width represented by the angle, A. The image capture device may also have an imaging sensor with a width, W. Using these known quantities, a mapping between the visual direction of any visible feature, from the user's perspective, and the position in the image, can be obtained. The relationship between F, A and W is illustrated in the top diagram 510. It will be understood that the angular width of the field of view of the camera is projected onto the imaging sensor (e.g. the charge coupled device of a digital camera) such that the mapping between A and W is determined by the focal length of the camera, F.

The lower diagram 520 illustrated in FIG. 5 shows a top-down view in which an example mapping of a particular visual angle to a corresponding position on an image sensor is represented for the horizontal direction. The relationship between the angular visual direction of the visual feature (illustrated by angle, D) and the position on the image sensor upon which that visual feature is focused (illustrated by the distance X from the centre of the image sensor) is provided using the equation $X = F \tan(D)$. Thus, by determining the obscured region associated with a particular viewer, this relationship enables a mapping to be determined corresponding to a list of the pixel positions whereby characteristics of the scene associated with the obscured region of a particular viewer will be captured by the imaging sensor. These co-ordinates can then be stored in memory and then recalled when required to allow generation of a viewer support image representative of the obscured region.

Figure 6:
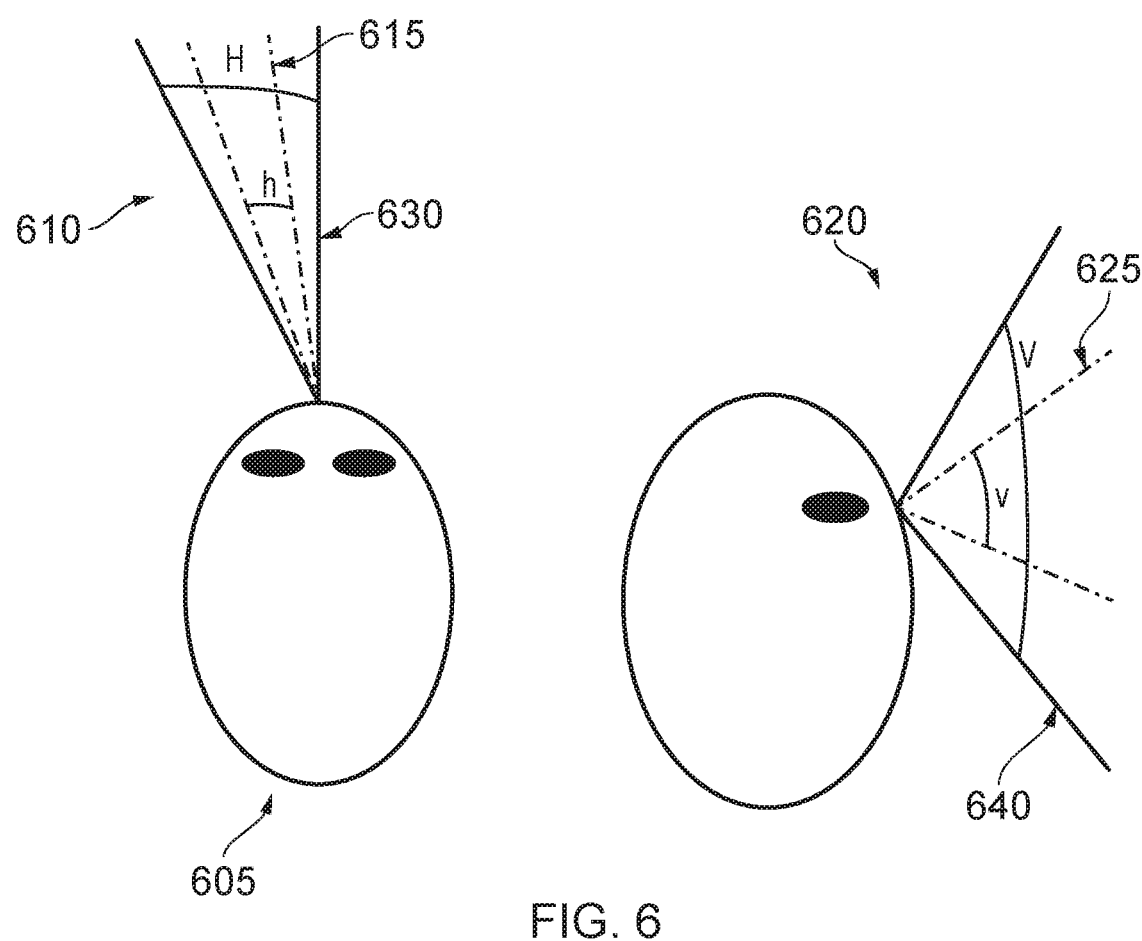
FIG. 6 illustrates an angular width in the horizontal and vertical directions of an obscured region of a viewer and an angular width for a viewer support image.

FIG. 6 illustrates an angular width in the horizontal 610 and vertical directions 620 of an obscured region of a viewer 605 and an angular width to be used for a viewer support image. As illustrated in FIG. 6, the obscured region 615 in an angular horizontal extent is indicated by angle, h and the obscured region 625 in an angular vertical extent is indicated by angle, v.

As discussed above with respect to FIG. 5, via the mapping that has been generated for that viewer, these angular values will enable pixel locations on the sensor of the imaging device that captures the image of a scene being viewed by a viewer to be determined. In other words, the mapping may be used to calculate a subregion of the captured image that is to be used for the viewer support image and a processor may be configured to select a subset of image data associated with this subregion from the originally captured image. This mapping is stored in memory as a list of co-ordinates as has been previously described with respect to FIGS. 1 and 5. FIG. 6 also illustrates a horizontal areal extent 630 (indicated by H) and vertical areal extent 640 (indicated by V) that may be chosen when selecting a subset of image data for the viewer support image. These areal extents include the area corresponding to the obscured region 615, 625 but also includes a surrounding region as has been previously described with respect to FIG. 2. The surrounding region helps to provide the viewer with a contextual view of the obscured region. The pixel values associated with the surrounding region may also be determined via a mapping as illustrated in FIG. 5. These pixel values may also be stored as a list in memory that can be recalled when generating a viewer support image. As will be appreciated by the skilled person, the size of the surrounding region can be adjusted according to the desires of the viewer and may be any appropriate size. Alternatively, no image data corresponding to the surrounding region may be used when generating a viewer support image and only the data associated with the obscured region may be used.

Figure 7:
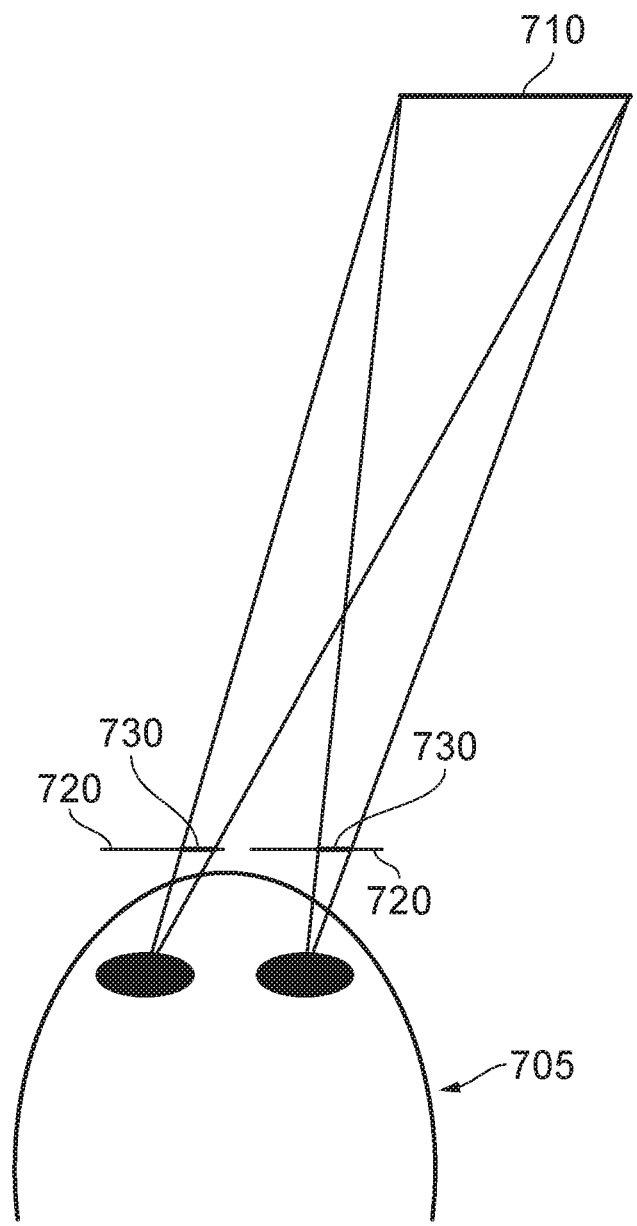
FIG. 7 illustrates positioning of a viewer support image on separate display screens located in front of a left and right eye of a viewer.

FIG. 7 illustrates positioning of a viewer support image on separate display screens located in front of a left and right eye of a viewer such that a perception of depth is provided. For example, binocular presentation of the viewer support image can be used to determine its apparent location in 3D space. The line 710 illustrates the perceived location of the viewer support image in 3D space (i.e. in their visual field). As can be seen in FIG. 7, this image appears at some distance from, and to the right of, the viewer 705. By tracing from the perceived location of the support image in 3D space to the viewer's left or right eye, a location on each display screen as illustrated in FIG. 7 is intersected allowing the appropriate location to display the support image on each screen to be determined. What this means is that the position and the visible area of the viewer support image may be different on the different display screens in front of the left and right eye. In other words, the viewer support images are displayed in different areas of the display screens in front of the left and the right eyes. The lines 720 show the display screens in front of a respective eye of the viewer. The lines 730 show the locations of the support images on the different display screens following the determination described above. It will be appreciated that this binocular presentation may also be achieved with a unitary display screen.

Figure 8:
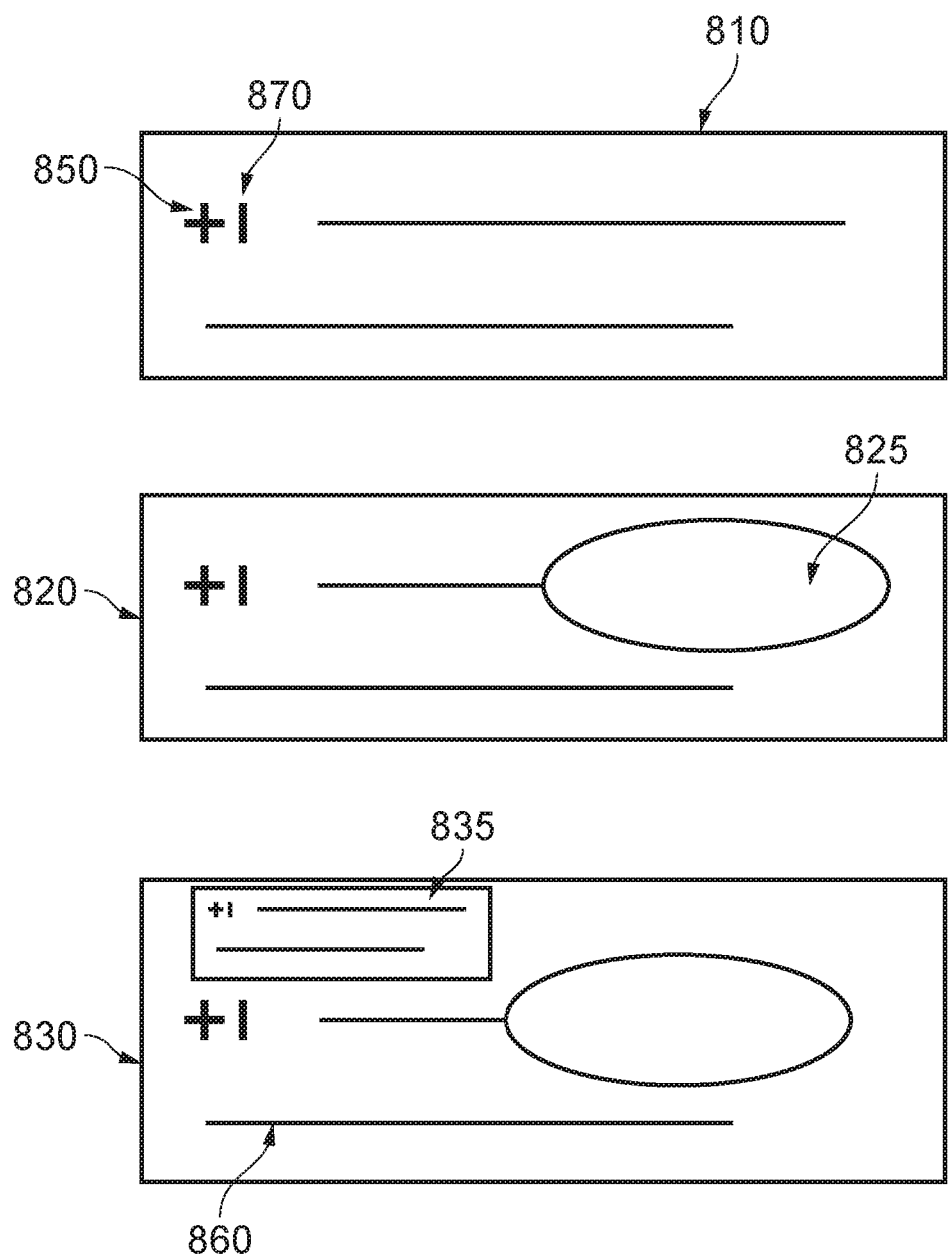
FIG. 8 illustrates an example including a set of screens presented to a viewer showing an unobscured screen, an obscured screen and an obscured screen with a viewer support image.

FIG. 8 illustrates an experimental example including a set of screens presented to a viewer showing an unobscured screen, an obscured screen and an obscured screen with a viewer support image. The experiment was carried out via using a simulated scotoma on participants with normal vision (by using eye tracking to blank out a region of their visual field). The presence of a viewer support image was also simulated. Performance was tested using a line bisection task, in which a line is presented on the screen and the observer indicates its perceived midpoint by moving a mouse cursor. This was chosen as a simple and well-established task used in understanding the effects of visual field loss in stroke. Three conditions were tested. In the baseline test 810, there was no artificial scotoma and no viewer support image. In the artificial scotoma test 820, a simulated scotoma 825 was created by masking a region of the visual field, which lays over a portion of the line to be bisected. In the artificial scotoma with viewer support image test 830, a windowed view 835 was provided in addition to the scotoma, so that the line (and a spatial reference) could be seen in full within the window. It was predicted that the performance of the viewer would be substantially impaired in the artificial scotoma test 820 relative to the baseline test 810, and that a return towards baseline test performance in the artificial scotoma with viewer support image test 830 should be expected. Prior to beginning the experiment observers were randomly allocated to a left-blind or right-blind group. On each trial, a fixation cross 850 was presented to the left of centre for the right-blind, and to the right of centre for left-blind conditions. The target line for each observer was always presented on the same side (either left or right). An additional reference line 860 was presented below the target. A small vertical cursor 870 was presented on the screen. On each trial the observer moved this cursor horizontally until they believed it appeared to bisect the target line. A range of target line lengths were presented (categorised as short, medium and long). Observers were required to keep their eyes fixated on the fixation cross. If they moved their gaze away, the target, reference and cursor all disappeared from view and they were not able to respond. The stimulus reappeared once the cross was re-fixated. In the scotoma test 820, a grey oval (with edges smoothed by a Gaussian luminance profile) was overlaid so as to obscure a proportion of the target line. The reference line was not obscured, but the cursor was not visible when it fell within the region of the artificial scotoma 825. In the test 830, the artificial scotoma was still present, and additionally an image of the target and references lines was presented above fixation. The cursor was not present in this viewer support window, to ensure that the task was completed in the stimulus space, rather than just in the window. The visibility of the reference in both the original space and the window allowed it to be used as a reference—within the window the observer should be able to see the length and location of the target (relative to the reference)—even if it was obscured by the artificial scotoma. All observers completed the baseline task first. Half of the observers then completed the artificial scotoma test followed by the artificial scotoma with viewer support image test whilst the other half of observers completed these tests in the opposite order.

Figure 9:
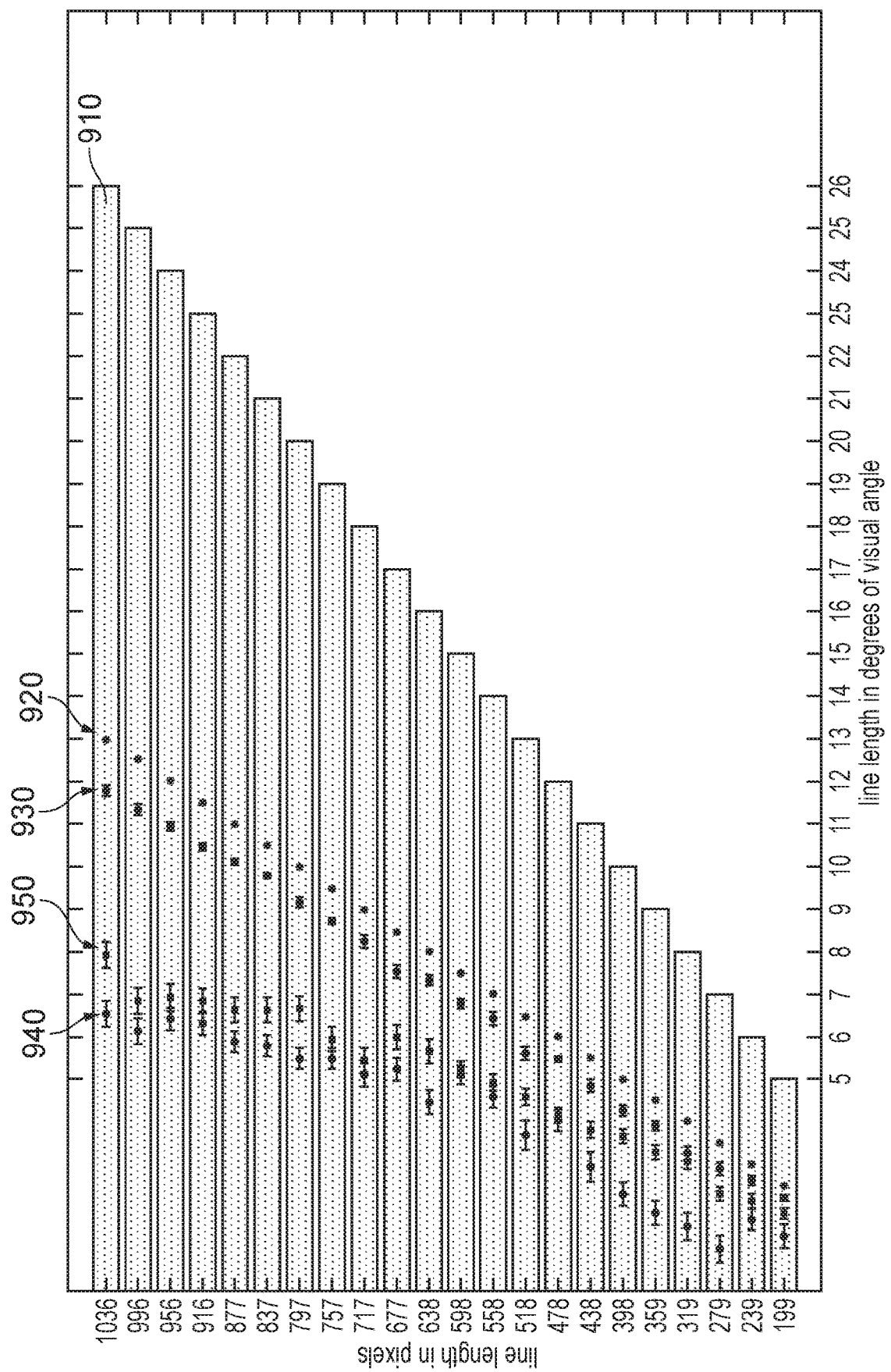
FIG. 9 illustrates results of carrying out the experimental example illustrated in FIG. 8.

FIG. 9 illustrates results of carrying out experimental example illustrated in FIG. 8. Each bar 910 represents the length of one of the target lines (with length in visual angle on the x-axis and length in on-screen pixels on the y-axis). The rightmost starred markers 920 indicate the true centre of each line. The circular data points 930 that are proximate to the starred markers 920 for each line length show the average deviation from perfect performance in the baseline test of FIG. 8. The circular data points 940 on the left-most side of the graph show performance in the artificial scotoma test of FIG. 8. The data points 940 are substantially further away from the true values than in the baseline condition 930, indicating the large errors resulting from the artificial scotoma. The square data points 950 indicate the performance in the artificial scotoma and viewer support image test of FIG. 8. These were predicted to lie between the circular points 940 and circular points 930 (return to baseline performance). An improvement in performance was found with all line lengths, with the viewer support image being particularly effective in the near periphery (i.e. for the shortest lines).

In view of the above, it will be appreciated that there are a number of differences in this approach that help to provide benefits over prior art approaches. For example, according to certain embodiments of the present invention there may be no optical distortion of the image. Also, the viewer support image will be seen as a distinct object (i.e. a projection screen or "window") in its own right, with a clearly specified location in 3D space. This is of benefit when compared with the combination of remapping of the field, and visual confusion, which characterise the effects of prisms. Furthermore, the transparency of the support image can be manipulated in real time. This helps to allow both the display screen and the real world to be seen in the same visual direction (and without spatial confusion since binocular disparity will unambiguously define the location of the screen in 3D space). Additionally, the support image can be moved around in real time to suit each user, the image can be magnified within the display screen, and the support image can be called up and dismissed on demand, so that it can be removed when it is disrupting visual cognition. Also the presence of both seen and unseen information makes the mapping to understand the location of the otherwise unseen objects relatively straightforward (in the same way that we can piece together our views through the windscreen and through the rear view and wing mirrors, and use this to be confident also about the remaining blind spots). There is also the ability to help provide enhancements to the image rather the provide a simple replica—so that, in particular, contrast can be enhanced, and machine vision and AI can be used to detect edges and segment the scene and highlight the salient segmenting edges. Hazard detection and warning (for example to warn of rapidly moving objects such as vehicles) can also be built into the software.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method for providing a viewer having a visual field defect with a visual aid, comprising:
    capturing at least one image of a scene via at least one image capture device supported by a headset worn by the viewer;
    accessing at least one memory element which stores one or more records representing a set of co-ordinates for the visual field defect;
    selecting, from image data associated with the at least one image, a subset of image data based on the set of co-ordinates indicative of characteristics of the scene within the visual field defect;
    displaying at least one viewer support image, generated based on the selected subset of image data, on at least one display screen supported by the headset and provided in front of the viewer, wherein the at least one viewer support image corresponds to a subregion of the at least one image;
    displaying the viewer support image on a first display screen or a first region of a unitary display screen located in front of the viewer's left eye and a second display screen or a second region of the unitary display screen located in front of the viewer's right eye; and
    displaying the viewer support image in a different area of the first and second display screens or of the first and second regions of the unitary display screen such that a perception of depth is provided;
    wherein the viewer support image appears in a predetermined area in the visual field spaced apart from and outside of the visual field defect.

2. The method of claim 1, wherein the visual field defect is a blurred region or a blind region in the visual field.

3. The method of claim 1, further comprising:
    determining the predetermined area responsive to a preselected input of the viewer.

4. The method of claim 1, further comprising:
    selecting the subset of image data responsive to accessing at least one memory element which stores one or more records representing a set of co-ordinates for the visual field defect.

5. The method of claim 1, wherein a transparency of the viewer support image is adjustable between a value of 0% and 100%.

6. The method of claim 1, further comprising:
    displaying the image of the scene on the display screen such that the image occupies substantially all of the visual field; and
    overlaying the viewer support image on the displayed image of the scene.

7. The method of claim 1, further comprising:
    displaying the viewer support image on at least one partially transparent display screen such that a remaining visual field outside of an area associated with the viewer support image in the visual field is provided via a direct line-of-sight between an eye of the viewer and the scene.

8. A non-transitory computer readable medium comprising instructions which, when executed by a computer, cause the computer to carry out the method of claim 1.

9. The method of claim 1, further comprising:
    automatically determining at least one region of the at least one image of the scene outside of the visual field defect where there are no or only few features of interest; and
    displaying the viewer support image in said at least one region.

10. The method as claimed in claim 9, further comprising: dynamically re-positioning the viewer support image in real-time as the viewer changes their visual field.

11. An apparatus for providing a viewer having a visual field defect with a visual aid, comprising:
    at least one image capture device, supported by a headset worn by the viewer, configured to capture at least one image of a scene;
    at least one memory element which stores one or more records representing a set of co-ordinates for the visual field defect;
    at least one processor configured to access the at least one memory element and select, from image data associated with the at least one image, a subset of image data based on the set of co-ordinates indicative of characteristics of the scene within the visual field defect; and
    at least one display screen that displays at least one viewer support image, generated based on the subset of image data, wherein the display screen is supported by the headset and is provided in front of the viewer, and wherein the viewer support image corresponds to a subregion of the at least one image;
    wherein:
    the viewer support image is displayed on the display screen in a predetermined area in the visual field spaced apart from and outside of the visual field defect;
    the viewer support image is displayed on a first display screen or a first region of a unitary display screen located in front of the viewer's left eye and a second display screen or a second region of the unitary display screen located in front of the viewer's right eye; and the viewer support image is in a different area of the first and second display screens or the first and second regions of the unitary display screen such that a perception of depth is provided.

12. The apparatus of claim 11, wherein the visual field defect is a blurred region or a blind region in the visual field.

13. The apparatus of claim 11, wherein the processor is configured to select the subset of image data indicative of characteristics of the scene within the visual field defect and in at least one surrounding region in the visual field that at least partially surrounds the visual field defect.

14. The apparatus of claim 11, wherein: the display screen displays the image of the scene such that the image occupies substantially all of the visual field; and the viewer support image is overlaid on the displayed image of the scene.

15. The apparatus of claim 11, wherein the display screen is at least partially transparent and displays the viewer support image such that a remaining visual field outside of an area associated with the viewer support image in the visual field is provided via a direct line-of-sight between an eye of the viewer and the scene.

* * * * *